United States Patent [19]

McBean

[11] Patent Number: 5,377,128

[45] Date of Patent: Dec. 27, 1994

[54] SELF-CALIBRATING INSTRUMENTATION SYSTEM WITH MULTIPLE SENSOR MODULES

[76] Inventor: Ronald V. McBean, 891 S. Paradise Dr., Gilbert, Ariz. 85233

[21] Appl. No.: 132,848

[22] Filed: Oct. 5, 1993

Related U.S. Application Data

[62] Division of Ser. No. 982,309, Nov. 25, 1992.

[51] Int. Cl.$^5$ ............................................. G06F 13/00
[52] U.S. Cl. ........................ 364/571.04; 364/571.01; 364/571.02; 364/571.07; 73/1 R
[58] Field of Search ........... 364/550, 557, 558, 571.01, 364/571.02, 571.03, 571.04, 571.07; 73/1 R

[56] References Cited

U.S. PATENT DOCUMENTS

| | | | |
|---|---|---|---|
| 3,988,577 | 10/1976 | Leitner | 235/151.1 |
| 4,573,133 | 2/1986 | White | 364/571 |
| 4,622,644 | 11/1986 | Hansen | 364/559 |
| 4,641,249 | 2/1987 | Gion et al. | 364/496 |
| 4,669,052 | 5/1987 | Bianco | 364/571 |
| 4,674,061 | 6/1987 | Diskowski et al. | 364/571 |
| 4,695,955 | 9/1987 | Faisandier | 364/571 |
| 4,716,536 | 12/1987 | Blanchard | 364/571 |
| 4,800,513 | 1/1989 | Deutsch | 364/571.02 |
| 4,831,866 | 5/1989 | Forkert et al. | 73/3 |
| 4,858,145 | 8/1989 | Inoue et al. | 364/506 |
| 4,858,161 | 8/1989 | Baumann | 364/571.03 |
| 4,866,640 | 9/1989 | Morrison, Jr. | 364/558 |
| 4,873,655 | 10/1989 | Kondraske | 364/553 |
| 4,890,246 | 12/1989 | Oldendorf et al. | 364/567 |
| 4,895,454 | 1/1990 | Kammleiter et al. | 374/163 |
| 4,909,338 | 3/1990 | Vitunic et al. | 177/50 |
| 4,910,519 | 3/1990 | Duell et al. | 341/157 |
| 4,912,468 | 3/1990 | Rust | 341/119 |
| 4,926,364 | 5/1990 | Brotherton | 364/581 |
| 4,930,095 | 5/1990 | Yuchi et al. | 364/571.01 |
| 4,931,967 | 6/1990 | Boe et al. | 364/571.01 |
| 4,937,764 | 6/1990 | Komatsu et al. | 364/558 |
| 4,972,333 | 11/1990 | Isikawa | 364/571.07 |
| 5,008,843 | 4/1991 | Poelsler et al. | 364/571.02 |
| 5,089,979 | 2/1992 | McEachern et al. | 364/571.04 |
| 5,121,051 | 6/1992 | Steinbrecher et al. | 364/571.03 |

*Primary Examiner*—Emanuel T. Voeltz
*Assistant Examiner*—Craig Steven Miller
*Attorney, Agent, or Firm*—Cahill, Sutton & Thomas

[57] ABSTRACT

An instrumentation system includes a hand-held computer-based measuring meter having a visual display and a plurality of individual sensor modules that can be selectively coupled to the measuring meter for measuring one of a variety of parameters such as temperature, pressure, or the like. Each sensor module includes a sensor responsive to a particular stimulus, as well as a data memory for storing information about the sensor. When the sensor module is interconnected with the measuring meter, the measuring meter accesses the memory of the sensor module to input data corresponding to sensor type, an accuracy code, calibration point data, and a calibration date code. The measuring meter compares the calibration date code to the current date to determine whether the sensor module requires recalibration. The measuring meter uses the accuracy code data to determine the number of significant digits displayed by the visual display. The measuring meter uses the sensor type code and calibration points to calibrate the measuring meter relative to the sensor module and to select the algorithm used to compute the current value measured by the sensor module.

5 Claims, 5 Drawing Sheets

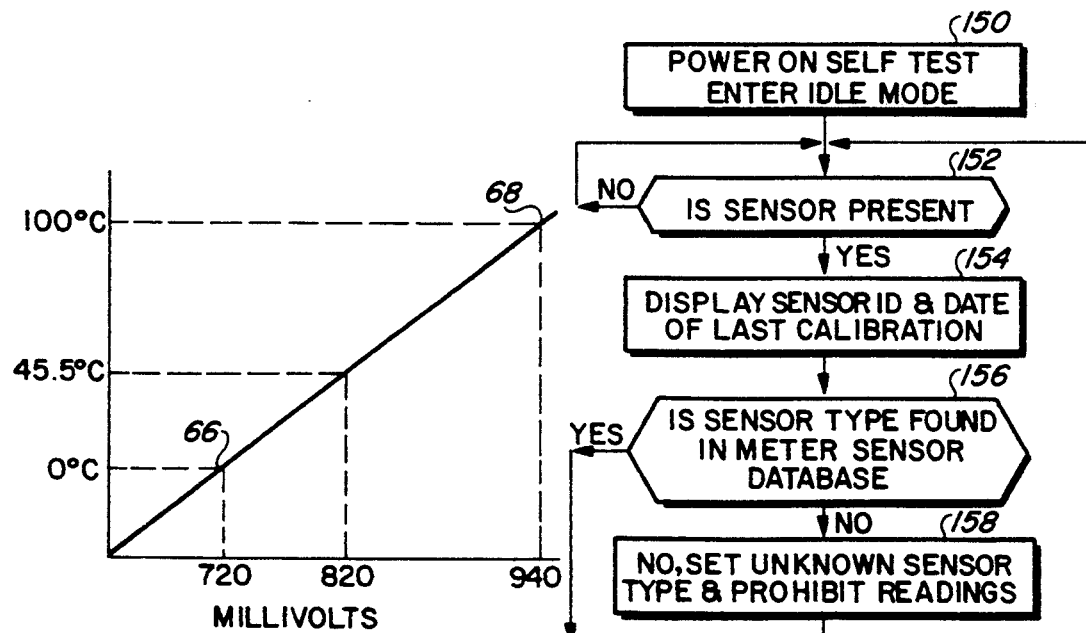
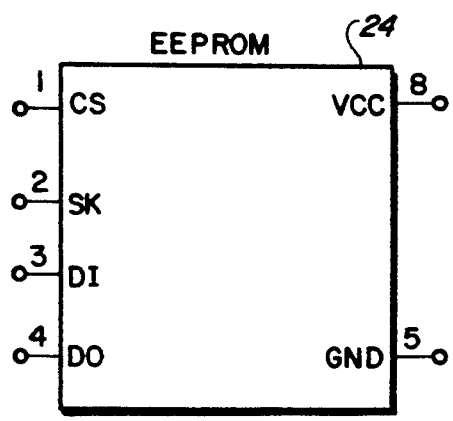
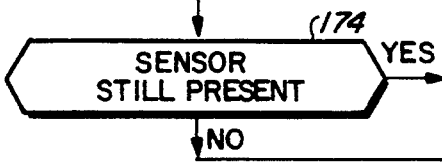

SELF-CALIBRATING INSTRUMENTATION SYSTEM WITH MULTIPLE SENSOR MODULES

This is a division of application Ser. No. 07/982,309 filed Nov. 25, 1992.

BACKGROUND OF THE INVENTION

1. Field of the Invention

The present invention relates generally to measuring instruments for measuring voltages, temperature, pressure, sound intensity, illumination, or the like, and more particularly, to a instrumentation system using a common measuring meter in conjunction with a plurality of different sensor modules for allowing the common measuring meter to measure a wide variety of test parameters.

2. Description of the Prior Art

Electronic measuring instruments are commonly used to measure and display a wide variety of parameters, such as voltages, temperature, pressure, speed, frequency, acceleration, sound intensity, and illumination levels, to name a few. Such measuring instruments commonly include a sensor which generates an analog signal having a magnitude that varies in accordance with variations in the parameter being measured. While such analog signals can be used to directly drive analog display meters, it is now common to convert the analog signal, using an analog-to-digital converter, to a digital signal that can be displayed digitally on a display panel.

Assuming that an engineer or technician is required to measure a variety of different parameters, such person ordinarily requires a corresponding number of measuring instruments. However, the cost of maintaining a separate measuring instrument for each type of parameter to be measured can be significant.

In addition, many electronic measuring instruments in use position a gain amplifier between the sensor and the analog-to-digital converter. Often the gain amplifier must be calibrated for zero signal strength (offset adjustment) and full scale signal strength (gain adjustment) before reliable measurement readings can be taken.

Most electronic measuring instruments must be recalibrated periodically to ensure accurate measurements. A calibration lab will keep a log of the date each measuring instrument has been calibrated and the date on which calibration is next due. However, unless someone remembers to check the calibration log periodically, it sometimes happens that instruments continue to be used beyond the scheduled recalibration due date.

Different measuring instruments may have different degrees of accuracy depending upon the type of parameter being measured. Even among two or more instruments intended to measure the same parameter, the responsiveness and accuracy of the sensing elements of such instruments can vary widely. Yet, the digital displays associated with such instruments may display the resulting measurement in digital format using a greater number of digits than are actually significant digits within the accuracy of the particular sensing element being used.

Particular types of sensing elements can produce electrical signals representing the measured parameter that vary in different ways for a given change in the parameter being measured. For example, a temperature sensitive element might produce an electrical voltage that varies linearly with changes in the temperature being measured. In contrast, a pressure sensitive element might produce an electrical resistance that varies in accordance with a quadratic formula. Accordingly, for a measuring meter designed to be used with different types of sensors, it is advantageous to know the type of sensor that is in use at any particular time in order to determine the best algorithm for computing the measured value.

Accordingly, it is an object of the present invention to provide an instrumentation system that includes a measuring meter adapted to be used with a plurality of sensor modules for allowing the measuring meter to compute and display a variety of measured parameters.

Another object of the present invention is to provide such an instrumentation system which automatically calibrates the measuring meter depending upon the particular sensor module being used with the measuring meter.

Still another object of the present invention is to provide such an instrumentation system wherein the measuring meter displays a warning legend if the selected sensor module is due for calibration.

A further object of the present invention is to provide such an instrumentation system wherein the measuring meter can detect the type of sensor coupled thereto for determining the algorithm used to compute the measured value of the parameter being sensed by the sensor module.

Yet another object of the present invention is to provide such an instrumentation system wherein the measuring meter can detect the range of accuracy of the sensor coupled thereto for determining the number of significant digits to display when displaying the computed measured value.

These and other objects of the present invention will become more apparent to those skilled in the art as the description thereof proceeds.

SUMMARY OF THE INVENTION

Briefly described, and in accordance with a preferred embodiment thereof, the present invention relates to an instrumentation system including a measuring meter including a central processor for computing a measurement of one or more parameters such as temperature, pressure, voltage or the like. A display is coupled to the central processor for numerically displaying the measurement computed by the central processor. The instrumentation system also includes two or more sensor modules, each sensor module being designed to sense a parameter such as temperature, pressure, voltage or the like, and to provide an output signal indicative of the parameter being sensed. A coupling mechanism is provided for selectively coupling one of the sensor modules to the measuring meter to measure and display the parameter being sensed by the selected sensor. The coupling mechanism couples the output signal provided by the selected sensor module to the measuring meter. In addition, the coupling mechanism also provides supplemental information to the measuring meter, as described below.

In a first embodiment, each sensor module provides calibration data to the measuring meter for indicating at least one previously determined output signal value at a known calibrating condition. This calibration data is provided via the coupling mechanism to the central processor of the measuring meter to calibrate the measuring meter to the selected sensor module. Each sensor module includes a memory on-board for storing at least one, but preferably two or more, calibration data values corresponding to output signals generated by the sensor module when exposed to the sensed parameter at fixed points. For example, if the selected sensor module is a temperature sensor, its on-board memory might store output values generated by the sensor module when exposed to known temperatures of 0 degrees Centigrade and 100 degrees Centigrade, respectively. The measuring meter accesses the previously stored calibration data values from the sensor module memory and uses such information to calibrate the measuring meter in accordance with the particular sensor module that has been selected. Such calibration data values can be used by the measuring meter to interpolate a measured value corresponding to the present output signal generated by the sensor module. The memory on-board each sensor module is preferably an electrically erasable, programmable memory (EEPROM) for allowing the calibration data values to be recalibrated at desired intervals.

In the preferred embodiment of the present invention, the sensor modules also include a mechanism for indicating to the measuring meter the type of sensor being used. For example, each sensor provides a sensor type code that is coupled by the coupling mechanism from the sensor module to the central processor for identifying the type of sensor module that has been coupled to the measuring meter, and hence, the type of condition sensed by the sensor included in each such sensor module. In turn, the central processor is responsive to the sensor type code of the selected sensor module for controlling the manner by which the central processor computes the measurement sensed by the selected sensor module. For example, if the central processor decodes the sensor type code as indicating that the selected sensor module is a temperature sensor, it might then select a linear interpolation algorithm for computing the measured value relative to the known data calibration values accessed from the memory of the selected sensor module. The aforementioned sensor type code can, if desired, be stored within the memory of the sensor module.

Another aspect of the present invention is to provide an instrumentation system wherein the user is warned if the sensor module is due for calibration. The central processor of the measuring meter includes a mechanism, such as a clock, for tracking the present date. Each of the sensor modules stores a calibration date code in its on-board memory for providing to the central processor information which the central processor can compare to the present date for detecting that the selected sensor module requires recalibration. The central processor reads the calibration date code from the memory of the selected sensor module for comparing the information provided thereby to the present date, and causing the display to display a warning message if the selected sensor module requires recalibration. The memories on-board each sensor module are preferably electrically erasable programmable memories (EEPROMS) for allowing the calibration date code data in the memory of each sensor module to be revised each time the sensor module is recalibrated. In some instances, the central processor is responsive to both the date code data and the sensor type code for determining whether calibration is due. For example, the calibration date code data might be stored as the date of the last calibration, and the sensor type code might determine when the next calibration is due.

Still another aspect of the present invention relates to the ability of the measuring meter to control the number of significant digits shown on the display panel of the measuring meter in accordance with the accuracy of the selected sensor module. Each sensor module includes an accuracy code for indicating to the central processor the degree of accuracy of the sensor included in each such sensor module. The central processor is responsive to the accuracy code of the selected sensor module for causing the display panel to indicate the accuracy of the measurement sensed by the selected sensor module, as by displaying only the number of significant digits within the range of accuracy of the selected sensor module. Preferably, the accuracy code is stored within the EEPROM memory on-board the sensor module for being accessed by the central processor.

BRIEF DESCRIPTION OF THE DRAWINGS

FIG. 2 is a graph illustrating a linear interpolation method of computing a measured temperature value based on digital values previously measured at calibration points of 0 degrees Centigrade and 100 degrees Centigrade.

FIG. 4 is a more detailed block diagram of the input and output terminals associated with the EEPROM shown in FIG. 3 .

FIG. 11 is a flow diagram schematically illustrating the steps performed by the instrumentation apparatus for accessing information from a selected sensor module and displaying the computed measured value on the display panel.

DETAILED DESCRIPTION OF THE PREFERRED EMBODIMENT

Figure 1:
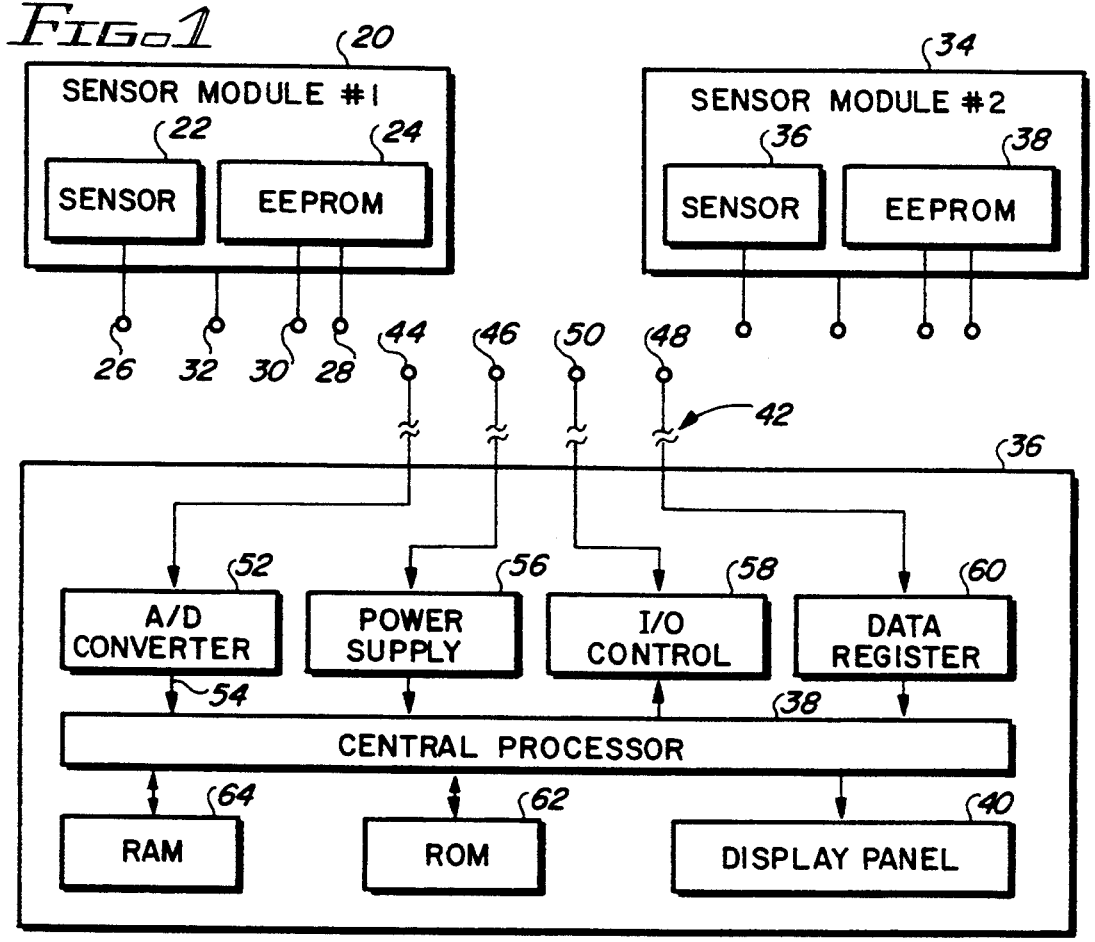
FIG. 1 is a simplified block diagram of an instrumentation system constructed in accordance with the teachings of the present invention and including a measuring meter and two sensor modules, and a connecting cable for coupling one of the sensor modules to the measuring meter.

An instrumentation apparatus constructed in accordance with a preferred embodiment of the present invention is generally illustrated in FIG. 1. A first sensor module 20 includes a sensor 22 and an electrically erasable programmable read only memory (or EEPROM) 24. Sensor 22 is responsive to a first condition, such as temperature, pressure, strain, voltage, current, frequency, flow, or the like, for generating an electrical signal indicative of such condition. This electrical signal is typically an analog voltage or current, and is provided on output terminal 26.

Still referring to FIG. 1, EEPROM 24 stores information in digital form about the sensor module, including the type of sensor, the date of last calibration, and one or more calibration points corresponding to a digital representation of the analog signal generated by sensor 22 at known calibration test conditions. EEPROM 24 may also store an identifying serial number to uniquely identify each sensor module, if desired. To minimize the number of data terminals extending from the sensor module, the EEPROM is preferably of the type which provides data serially as a clocked bit stream, rather than as parallel data bits. In FIG. 1, terminal 28 represents the serial data output terminal of EEPROM 24, while terminal 30 is the serial clock input terminal for receiving clock signals that control the sequencing of data output bits. Terminal 32 collectively represents power supply voltages and a constant current source required by sensor module 20 to operate correctly.

Also shown in FIG. 1 is a second sensor module 34; like sensor module 20, sensor module 34 includes a sensor 36 and an EEPROM 38. Sensor module 34 can, if desired, be of the same type of sensor as sensor module 20, i.e., it can be responsive to the same parameter measured by sensor module 20. Alternatively, sensor module 34 can be responsive to a different parameter; for example, sensor module 20 can be responsive to temperature, while sensor module 34 can be responsive to air pressure. As indicated in FIG. 1, sensor module 34 includes the same input/output terminals and power supply terminals as sensor module 20. While only two sensor modules 20 and 34 are illustrated in FIG. 1, those skilled in the art will appreciate that a great number and variety of sensor modules may be provided for use in the present instrumentation system.

Within FIG. 1, a measuring meter 36 is shown for computing and displaying a measurement based upon information received from a selected one of sensor modules 20 and 34. Measuring meter 36 includes a central processor 38 responsive to electrical signals generated by the selected sensor module for computing a measurement sensed by the selected sensor module. Measuring meter 36 also includes a display panel 40 coupled to the central processor 38 for numerically displaying the measurement computed by central processor 38. If desired, display panel 40 can also display alphanumeric characters indicating the serial number of the selected sensor module, the date of last calibration of the selected sensor module, a warning message that calibration of the sensor module is due, and the like.

A multiple conductor cable, designated generally within FIG. 1 by reference numeral 42, is provided for selectively coupling a selected one of sensor modules 20 and 34 to central processor 38 within measuring meter 36. Cable 42 includes a terminal 44 adapted to be coupled with terminal 26 of sensor module 20 to receive the analog output signal generated by sensor module 20. Cable 42 also includes a plurality of terminals 46 adapted to be coupled with terminals 32 of sensor module 20 to provide power supply voltages and a constant current source thereto. Cable 42 also includes a terminal 48 adapted to be coupled with terminal 28 of sensor module 20 for receiving the serial data output from EEPROM 24. Cable 42 also includes a terminal 50 adapted to be coupled with terminal 30 of sensor module 20 for providing the serial clock signals that control the sequencing off data output bits from EEPROM 24.

As shown in FIG. 1, measuring meter 36 includes an analog-to-digital converter 52 electrically coupled with terminal 44 of cable 42 for converting the analog output signal generated by the selected sensor module into a corresponding digital value that can be operated upon by central processor 38. Analog-to-digital converter 52 is preferably of the type commercially available from National Semiconductor Corporation under Model Number ADC1225, which produces a twelve bit digital signal responsive to the analog input signal. The digital output of analog-to-digital converter 52 is coupled to a data bus 54 of central processor 38 for providing thereto the digital representation of the analog input signal.

Measuring meter 36 also includes a power supply block 56 which includes a power source, voltage regulators, and a constant current source. The regulated voltages are used both within measuring meter 36, as well as by the selected sensor module. The constant current source is used by the selected sensor module to generate the analog sensor signal. Measuring meter 36 also includes a clock 58 for generating the synchronizing clocking signals supplied to the selected sensor module for accessing data stored in the EEPROM of the selected sensor module. In addition, measuring meter 36 includes a data register 60 for temporarily storing the serial data output from the EEPROM of the selected sensor module. As also shown in FIG. 1, central processor 38 is coupled with a read-only-memory (ROM) 62 which stores instructions for controlling operation of central processor 38, as well as a random-access-memory (RAM) 64 for providing working storage.

As indicated above, one of the aspects of the present invention relates to the self-calibrating feature of the present instrumentation system. The manner in which this self-calibrating feature operates will now be described with reference to FIGS. 1 and 2. For purposes of explanation, it will be assumed that sensor module 20 is the selected sensor module, and that it is a temperature sensor. During initial calibration of sensor module 20, it is determined that when the sensor module is exposed to a temperature of 0 degrees Centigrade, sensor 22 generates an analog output signal of 720 millivolts; it will be further assumed that an analog output signal of 720 millivolts causes an analog-to-digital converter of the type included in measuring meter 36 to produce a digital signal of "720" (or "001001010000" as a twelve-bit binary word). During calibration, the digital signal "720" is stored in EEPROM 24 as a first calibration point.

Similarly, during initial calibration of sensor module 20, it is determined that when the sensor module is exposed to a temperature of 100 degrees Centigrade, sensor 22 generates an analog output signal of 940 millivolts; it will be further assumed that an analog output signal of 940 millivolts causes an analog-to-digital converter of the type included in measuring meter 36 to produce a digital signal of "940" (or "001110101100" as a twelve-bit binary word). During calibration, the digital signal "940" is stored in EEPROM 24 as a second calibration point. Within the graph of FIG. 2, the known conditions at 0 degrees Centigrade and 100 degrees Centigrade are shown as calibration points 66 and 68, respectively, along with their corresponding digital values. These first and second calibration points are accessed from EEPROM 24 by central processor 36 when sensor module 20 is coupled to measuring meter 36.

In a manner to be described below, central processor 36 also detects from information supplied by EEPROM 24 that sensor module 20 is a temperature sensor, and that its output varies essentially linearly with changes in temperature. It is then a simple matter for central processor 38 to compute the measured value for the temperature based upon the digital value output by analog-to-digital converter 52 derived from the analog output signal supplied by sensor module 20 when actual measurements are being made. Central processor 38 merely interpolates the temperature corresponding to the present digital value based upon the known first and second calibration points. For example, if $D_x$ represents the digital value produced by analog-to-digital converter 52 for a current measurement, $D_0$ represents the digital value at 0 degrees Centigrade, and $D_{100}$ represents the digital value at 100 degrees Centigrade, then the temperature $T_x$ to be displayed by display panel 40 is computed by central processor 38 as follows:

$$T_x = 0° \text{ C.} + \{100° \text{ C.} \times [(D_x - D_0)/(D_{100} - D_0)]\}$$

Thus, in the example posed above, if $D_x$ for the current measurement is 820, as shown in FIG. 2, then $T_x =$ $$0° \text{ C.} + \{100° \text{ C.} \times [(820 - 720)/(940 - 720)]\}$$

$$= 0° \text{ C.} + \{100° \text{ C.} \times [(100)/(220)]\}$$

$$= 0° \text{ C.} + \{100° \text{ C.} \times [0.4545]\}$$

$$= 45.45° \text{ C., or } 45.5° \text{ C.}$$

as shown on FIG. 2.

In the manner just explained, the central processor 38 is responsive to the calibration data stored in EEPROM 24 of the selected sensor module 20 for calibrating the central processor 38 when computing the measurement sensed by the selected sensor module.

For sensors which produce other than a linear variation in output signal when the sensed parameter is varied, three or more calibration points can be stored in the EEPROM of each sensor module for allowing the central processor to select a curve-fitting algorithm that best fits the known calibration points, and then use the selected curve-fitting algorithm to compute the measured value for a current measurement. For example, pressure sensors may produce an output signal which varies according to a quadratic formula relative to variations in the pressure being sensed. In this event, upon detecting that the selected sensor module is a pressure sensor, central processor 38 might access three calibration points from the EEPROM of the selected sensor module and compute a quadratic formula based upon the three known calibration points. The central processor would then use the computed quadratic formula to convert subsequent measured digital values into pressure readings through interpolation.

Figure 3:
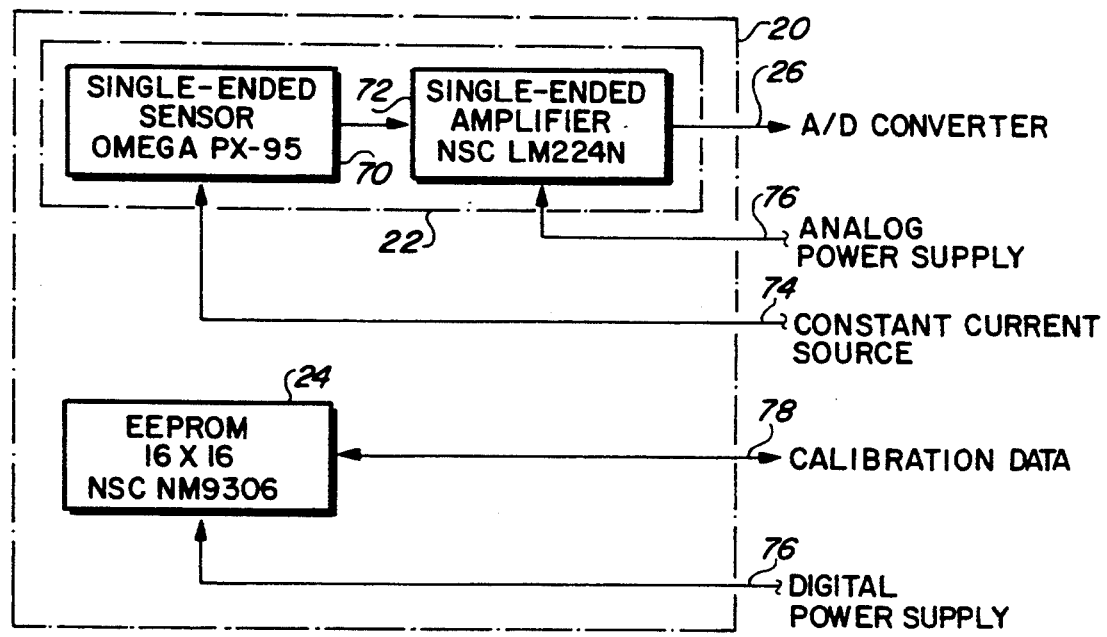
FIG. 3 is a more-detailed block diagram of a sensor module of the general type shown in FIG. 1, and including a sensor, amplifier, and EEPROM for storing information about the sensor.

FIG. 3 is a more detailed view of a typical sensor module used in the present instrumentation system. In FIG. 3, sensor 22 includes a single-ended output sensor 70 such as an Omega brand pressure sensor available under Part Number PX-95. Typically, such sensors develop a rather small signal range; accordingly, the output of sensor 70 is coupled to the input of an operational amplifier 72 for increasing the output signal strength of the analog output signal generated by sensor 70. Op amp 72 may be of the type commercially available from National Semiconductor Corporation as Model No. LM224N. The output of op amp 72 is coupled to the analog output terminal 26 of sensor module 20 for coupling with the analog-to-digital converter 52 in measuring meter 36.

Sensor element 70 requires a constant current source to produce analog output signals immune from variations in power supply voltage and the like. For this reason, sensor module 20 includes a constant current source terminal 74 which is supplied by cable 42 from power supply block 56 (see FIG. 1) with a constant current source independent of voltage or temperature fluctuations. Similarly, op amp 72 requires analog power supply voltages, including a regulated positive supply voltage and ground voltage; terminal 76 of sensor module 20 collectively represent such analog power supply voltages provided over cable 42 by power supply block 56 of measuring meter 36.

As shown in FIG. 3, sensor module 20 also includes EEPROM 24 which may be a sixteen word by sixteen bit (16×16) chip of the type commercially available from National Semiconductor Corporation under Model No. NM9306. This chip is shown in greater detail in FIG. 4, wherein chip pin 8 (Vcc) is the positive voltage supply, and chip pin 5 (GND) is the chip ground. These two chip pins are collectively shown in FIG. 3 by terminal 76 corresponding to the digital power supply. The EEPROM chip also includes a chip pin 1 that is a chip select (CS) control pin. The chip select signal is generated by the central processor and transmitted over cable 42 to the chip select (CS) control pin of the EEPROM to enable the EEPROM to transmit serial data to the central processor.

Still referring to FIG. 4, EEPROM chip 24 also includes a serial clock (SK) input pin 2 for receiving clocking signals that synchronize the transfer of data bits into and out of EEPROM 24. Chip pin 4 provides a serial data bit output stream of each of the sixteen bits making up each of the sixteen words stored therein. Chip pin 3 is used only during writing of data to EEPROM 24, as during initial calibration of sensor module 20, and during subsequent recalibration intervals. Chip pins 3 and 4 are collectively represented in FIG. 3 as calibration data terminal 78.

While not shown in FIGS. 1 and 3, sensor module 20 may also include additional binary output terminals. For example, in the preferred embodiment of the present invention, sensor module 20 includes an additional 11 binary terminals designated RSA, RSB, . . . ,through RSK. These additional eleven binary lines can be used, for example, to send an eleven-bit digital signal from sensor module 20 to the measuring meter, bypassing the analog-to-digital converter 52 within measuring meter 36 For example, sensor module 20 might include its own self-contained analog-to-digital converter. Alternatively, sensor module 20 may be counting the number of occurrences of a particular event during a given interval in order to indicate frequency, in which case, the output of sensor module 20 will be a digital output signal that can be sent as parallel data bits over terminals RSA-RSK to central processor 38. Moreover, not all of the binary lines need be used to transmit the digital output. For example, if sensor module 20 provides an eight-bit digital output signal, then such output signal can be conveyed by terminals RSA-RSH, while remaining terminals RSI-RSK may be used to send binary control signals, such as enabling the counter and clearing the counter.

In the preferred embodiment of the present invention, each sensor module has a total of 26 terminals defined as follows:

| Terminal | SENSOR MODULLE PINOUT Definition |
|---|---|
| 1 | V+ (7.2 v) for analog power supply |
| 2 | Vgnd (7.2 v) for analog power supply |
| 3 | Vcc (5 v) for digital power supply |
| 4 | Vend (5 v) for digital power supply |
| 5 | Sout sensor out (sensor analog output signal) |
| 6 | Sgnd sensor gnd (sensor analog output ground) |
| 7 | CC+ constant current source (positive) |
| 8 | CC− constant current source (negative) |
| 9 | CS chip select (CS pin to EEPROM) |
| 10 | SK serial clock (SK pin to EEPROM) |
| 11 | SO serial data out (DO pin from EEPROM) |
| 12 | SI serial data in (DI pin from EEPROM) |
| 13 | RSA reserved binary line |
| 14 | RSB reserved binary line |
| 15 | Sensor Present |
| 16 | RSC reserved binary line |
| 17 | RSD reserved binary line |
| 18 | RSE reserved binary line |
| 19 | RSF reserved binary line |
| 20 | RSG reserved binary line |
| 21 | RSH reserved binary line |
| 22 | RSI reserved binary line |
| 23 | RSJ reserved binary line |
| 24 | RSK reserved binary line |
| 25 | V−(−7.2 v) for double-ended sensor analog power supply |
| 26 | Vgnd (−7.2 v) for double-ended sensor analog power supply |

With respect to terminal 15 (Sensor Present) in the above table, this terminal is normally kept at a logic "1" by the sensor module; when the sensor module is uncoupled from the connector cable, the conductor in the coupling cable that normally connects with the Sensor Present terminal is pulled to ground or logic "0", thereby signalling to the central processor that a sensor module is no longer present.

With respect to terminals 25 and 26, some sensor modules may use differential sensors and differential amplifiers to generate the analog output signal. For example a differential sensor module might use an Omega PX-83A differential sensor to develop a differential output signal that is then amplified by a differential amplifier. In this event the differential amplifier may require both positive and negative analog power supply voltages.

With respect to the data stored within EEPROM 24, the sixteen words of data are allocated as follows:

| E²prom Calibration Data Format | |
|---|---|
| Sensor Type | - 1 word |
| Serial Number | - 2 words (8 hexadecimal nibbles) |
| Reserved | - 2 words |
| Date of Last calibration | - 2 words (yr, mon, day, hr, mins) |
| Calibration Points | - 9 words (4 bits number of point) (12 bit of raw ADC data) |

The Sensor Type word includes 16 bits; the first field of four bits identifies the family type of sensor (i.e., air pressure, water pressure, strain, temperature, voltage, current, frequency, interval, flow, etc.). The next four bit field of the Sensor Type word can be used to specify a particular class of sensor within the given family. For example, if one class of temperature sensor is able to provide greater accuracy than another type of temperature sensor, then the two sensors can be distinguished from each other by the four-bit class field. Similarly if one class of temperature sensor need not be calibrated as often as another, the class field can be used to distinguish such sensors from each other. If one temperature sensor is adapted to provide an analog output signal and another temperature sensor is adapted to provide a digital output signal, the class field can be used to distinguish such sensors. The remaining eight bits in the Sensor Type word can be used, if necessary, to further distinguish two sensors of the same family and class.

The two Serial Number words can be used, if desired, to uniquely identify each sensor module for purposes of inventory control and record-keeping, including calibration logging.

The two words used for calibration date code information, i.e., date of last calibration, store the calendar date, and if desired the time, when the sensor module was last calibrated. Based upon this information together with the Sensor Type code, the central processor can determine when the next calibration date is due and determine whether the sensor module is still reliable.

The nine words of calibration data stored in EEPROM 24 provide up to nine twelve-bit digital values corresponding to the digitally-converted value of the sensor output at up to nine known calibration points. The first four bit field of each calibration data word is used to identify which calibration point (e.g., first, second third , . . . ) to which the twelve-bit digital value corresponds. Thus, for example, in the example used above, the first four bits of the first calibration word might be "0001" designating the first calibration point followed by the twelve-bit field "001001010000", corresponding to the raw analog-to-digital value of "720". Likewise, the first four bits of the second calibration word might be "0010" designating the second calibration point, followed by the twelve-bit field "001110101100", corresponding to the raw analog-to-digital value of "940".

Figure 5:
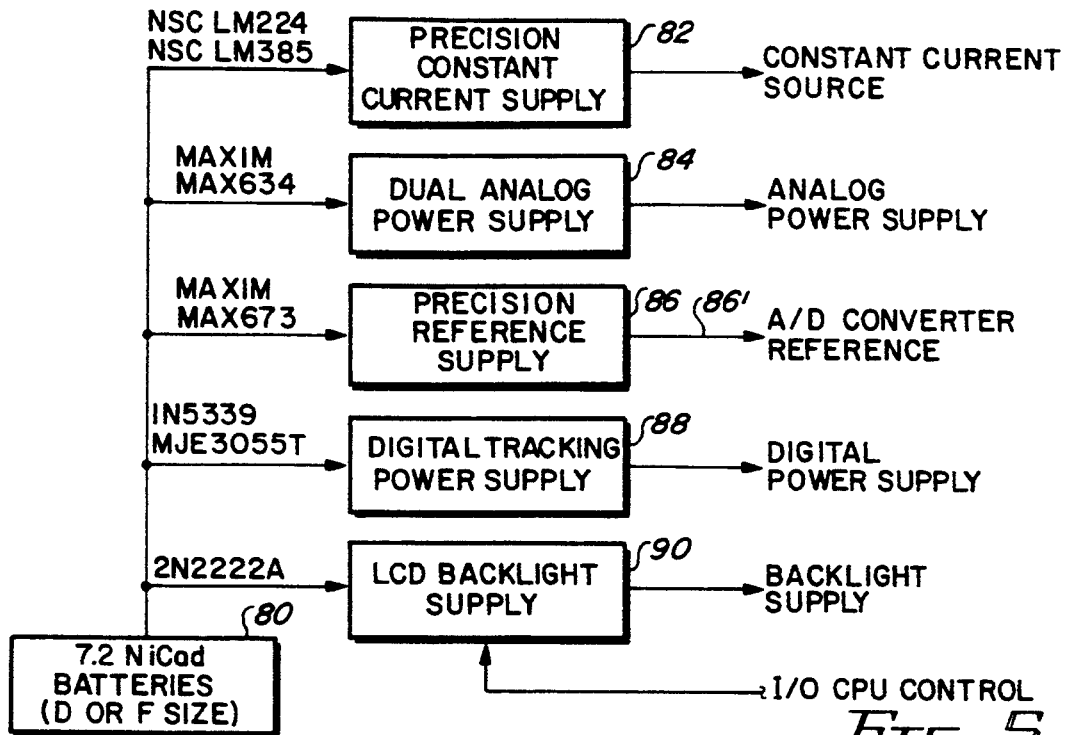
FIG. 5 is a block diagram of the power supply components included within the measuring meter for generating required voltages and a constant current source.

FIG. 5 shows in greater detail the power supply components collectively represented by power supply block 56 in FIG. 1. In FIG. 5, block 80 is a voltage supply including NiCad batteries which provide a voltage of approximately 7.2 volts. NiCad batteries are preferred to permit the instrumentation system to be used without attachment to an electrical outlet, and to lighten the weight of the measuring meter. Ideally, the measuring meter is provided as a hand-held unit.

The 7.2 volt output voltage provided by NiCad battery pack 80 is coupled to several power regulation blocks, including precision constant current supply 82, dual analog power supply 84, precision reference supply 86, digital tracking power supply 88, and LCD backlight supply 90. Precision constant current supply 82 includes a National Semiconductor Part Number LM385 voltage reference chip and a Part Number LM224 op amp for drawing a fixed current which is coupled through the connector cable 42 (see FIG. 1) to the selected sensor module. Dual analog power supply 84 includes a MAXIM brand voltage regulator of the type sold as Part Number MAX634, and generates regulated positive and negative 7.2 voltage sources relative to an analog ground. These analog power supply voltages are coupled over connector cable to the analog circuitry within the selected sensor module.

Precision reference supply 86 includes a MAXIM brand voltage reference source available as Part No.

MAX673 and provides a regulated voltage reference for the analog-to-digital converter 52 within measuring meter 36. Digital tracking power supply 88 includes an Intel IN5339 and an MJE3055T chip for producing a regulated power supply voltage for coupling to digital circuitry on-board the measuring meter 36, as well as to the EEPROM and any other digital circuitry on-board the selected sensor module. Finally, LCD backlight supply 90 produces a supply voltage for backlighting the LCD characters in display panel 40 (see FIG. 1).

Figure 6:
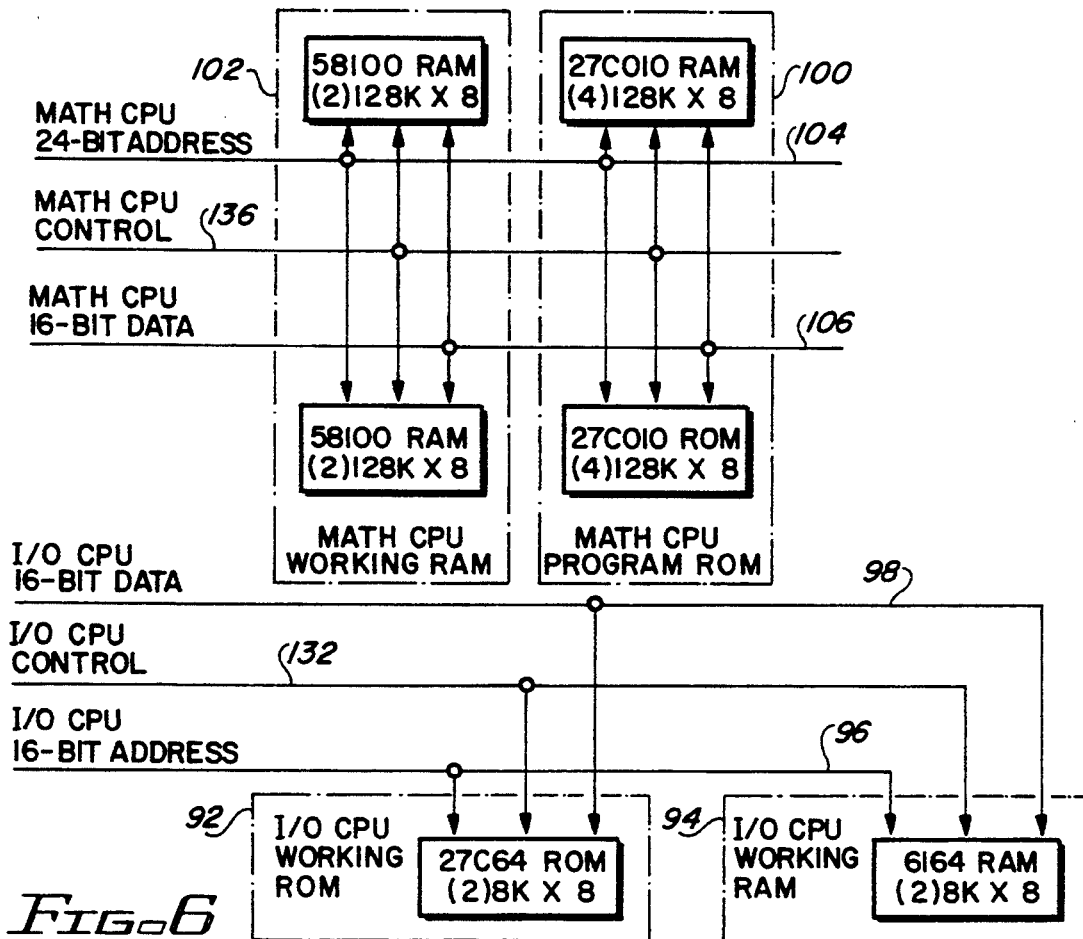
FIG. 6 is a block diagram of the memory block contained within the measuring meter, including ROM (read-only-memory) for controlling math operations and input/output operations, as well as RAM (random-access-memory) for temporarily saving working data.

FIG. 1 illustrates a single block 38 as the central processor. In the preferred embodiment of the present invention, there are actually two processing units, one being designated the math CPU and the second being designated the I/O CPU. As the names imply, the math CPU is used to process data and compute the measured value, whereas the I/O CPU is used to control the routing of data from the sensor module to the measuring meter and to control the flow of operations performed within the measuring meter. Referring to FIG. 6, the I/O CPU has access to an 8K×16-bit I/O program ROM 92 formed by two 27C64 ROM chips which store instructions to be performed by the I/O CPU. The I/O CPU also has access to an 8K×16-bit working RAM 94 formed by two 6164 RAM chips for storing addresses and data. The I/O CPU ROM 92 and RAM 94 are addressed by a 16-bit I/O CPU address bus 96 and 16-bit data words are routed along a 16-bit I/O CPU data bus 98.

The memory for the math CPU is also shown in FIG. 6. The math CPU has access to a 256K×32-bit program ROM 100 formed by eight 27C010 ROM chips which store instructions, addresses, data, and control signals for controlling the math CPU. The math CPU also has access to a 256K×16-bit random access memory 102 formed by four 58100 RAM chips for saving computed data. The math CPU ROM 100 and RAM 102 are addressed by a 24-bit math CPU address bus 104, and 16-bit data words are routed along a 16-bit math CPU data bus 106.

Figure 7:
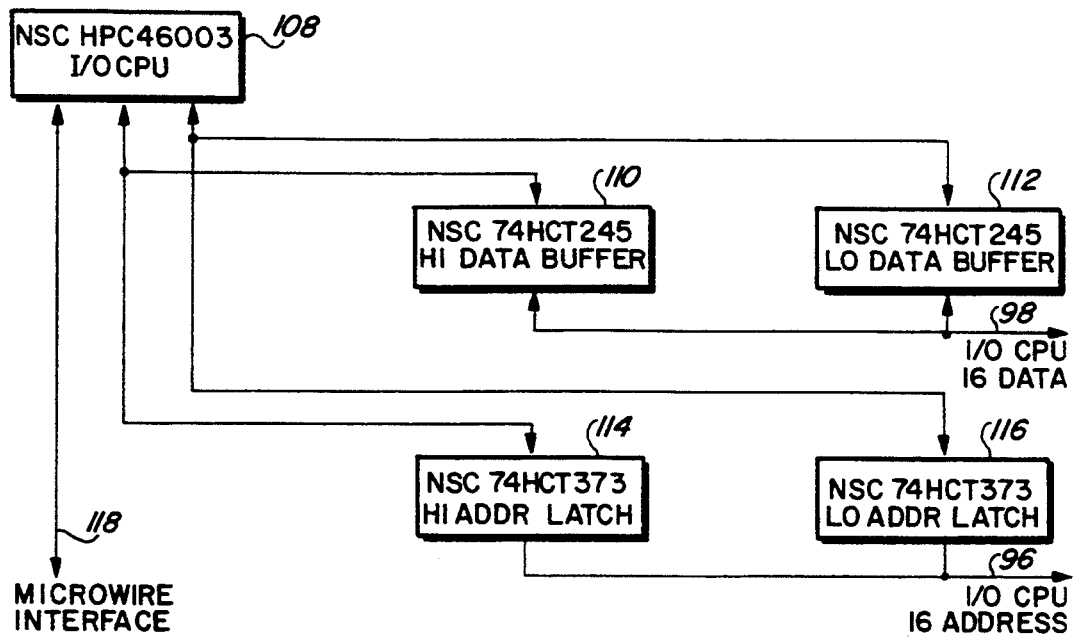
FIG. 7 is a block diagram of the input/output central processor used to control the routing of data and addresses in the central processor.

In FIG. 7, the I/O CPU itself is designated by reference numeral 108. Preferably, I/O CPU 108 is a National Semiconductor processor chip sold under Part Number HPC46003. The I/O CPU 108 interfaces with the 16-bit I/O CPU data bus 98 via a pair of data buffers 110 and 112, each of which is a National Semiconductor Part Number 74HCT245 chip. Such data buffers are bi-directional and can either send data from I/O CPU 108 to data bus 98, or vice versa. Addresses output by I/O CPU 108 are strobed into address latches 114 and 116 for transmission over I/O CPU address bus 96.

Also shown as both an input and an output to I/O CPU 108 is a series of control lines and data lines 118 collectively referred to as Microwire Interface. "Microwire" is a trademark of National Semiconductor Corporation for its method of microprocessor based serial communications and protocol. The National Semiconductor NM3906 EEPROM chips included in each of the sensor modules is essentially a Microwire peripheral, and the NM3906 EEPROM chips have internal components required to communicate serially in response to the Microwire interface control signals. For example; the microwire interface signals include the chip select (CS) and serial clock (SK) signals transmitted over cable 42 to the EEPROM of the selected sensor module.

Figure 8:
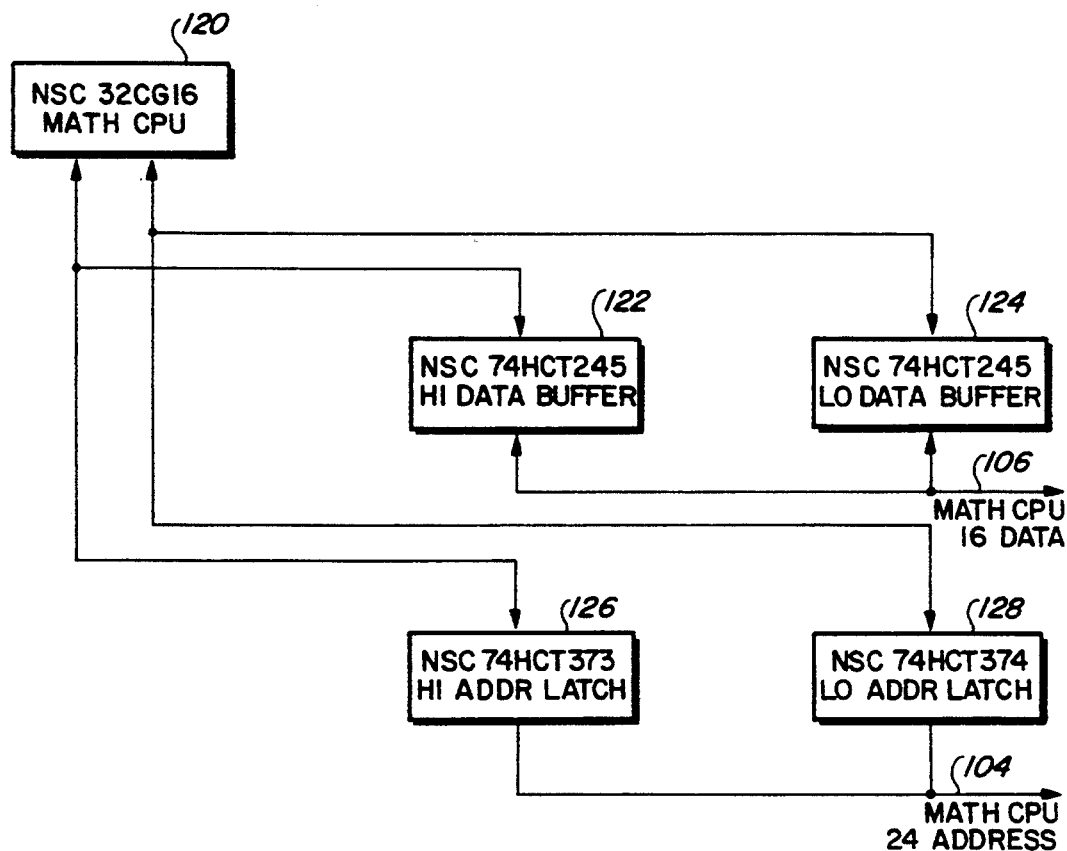
FIG. 8 is a block diagram of the math central processor used to control computational operations within the central processor of the measuring meter.

In FIG. 8, the math CPU 120 is shown. Math CPU 120 is preferably a National Semiconductor 32-bit processor available under Part No. 32CG16. The math CPU 120 interfaces with the 16-bit math CPU data bus 106 via a pair of data buffers 122 and 124, each of which is a National Semiconductor Part Number 74HCT245 chip. Such data buffers are bi-directional and can either send data from math CPU 120 to data bus 106, or vice versa. Addresses output by math CPU 120 are strobed into address latches 126 and 128 for transmission over math CPU address bus 104.

Figure 9:
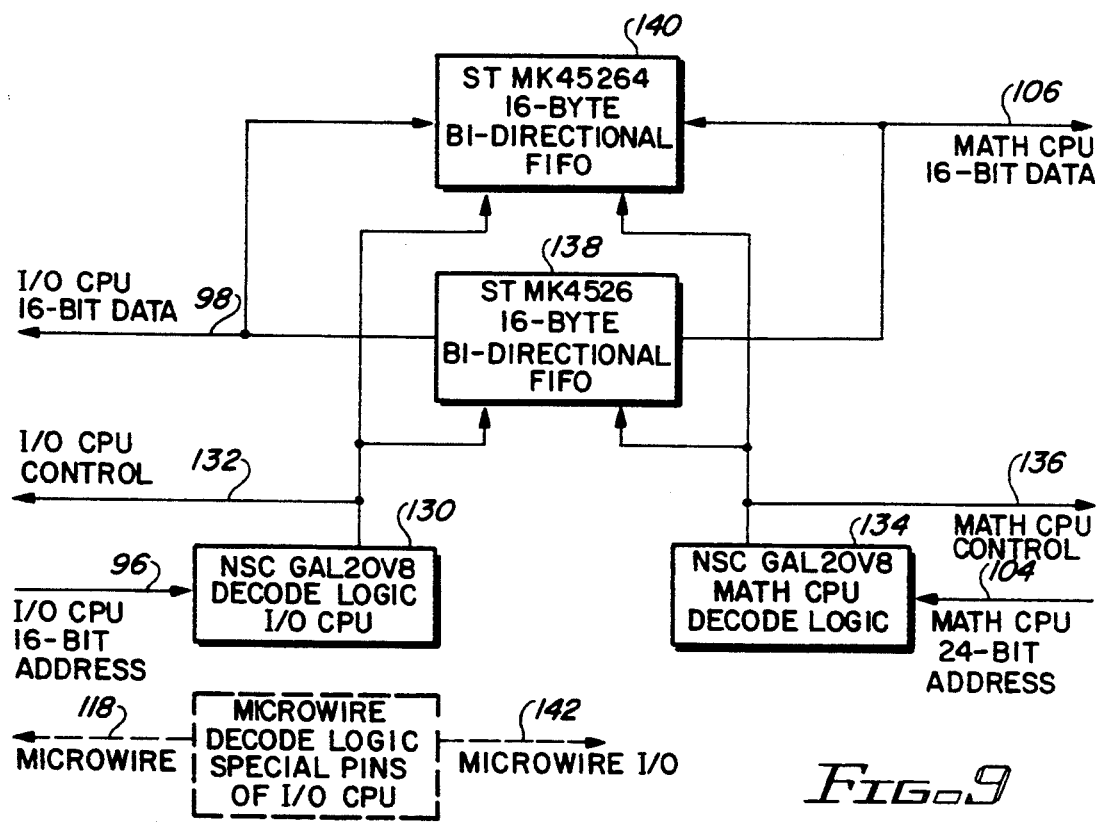
FIG. 9 is a block diagram of the input/output control logic.

FIG. 9 illustrates control logic used to control I/O CPU 108 and math CPU 120 and to allow the two CPUs to communicate with each other. Block 130 in FIG. 9 is a programmed gate array corresponding to National Semiconductor chip GAL20V8 which receives the 16-bit I/O CPU address and decodes the address to provide a series of I/O CPU control signals 132. These I/O CPU control signals 132 are routed to the I/O CPU memory (see FIG. 6) for controlling memory access. Similarly, block 134 in FIG. 9 is another programmed gate array corresponding to National Semiconductor chip GAL20V8 which receives the 24-bit math CPU address and decodes the address to provide a series of math CPU control signals 136. These math CPU control signals 136 are routed to the math CPU memory (see FIG. 6) for controlling memory access. Also shown in FIG. 9 are a pair of first-in; first-out (FIFO) bidirectional stacks 138 and 140 which allow the interchange of data between math CPU data bus 106 and I/O CPU data bus 98. Stacks 138 and 140 each hold 16 bytes of data and are preferably of the type commercially available from Thompson Electronics under Part Number ST MK45264. The control signals generated by gate array blocks 130 and 134 also control the flow of data onto and off of stacks 138 and 140.

Also shown in FIG. 9 is a Microwire decode logic circuit coupled to I/O CPU 108 for receiving the Microwire signals therefrom on lines 118, and for generating decoded Microwire control signals on lines 142.

The memory map for the I/O CPU memory is set forth in attached Appendix A in order to indicate the memory addresses used by I/O CPU 108. The manner by which the programmed gate array logic within I/O CPU decode logic block 130 accesses the I/O CPU memory is indicated in attached Appendix B.

Figure 10:
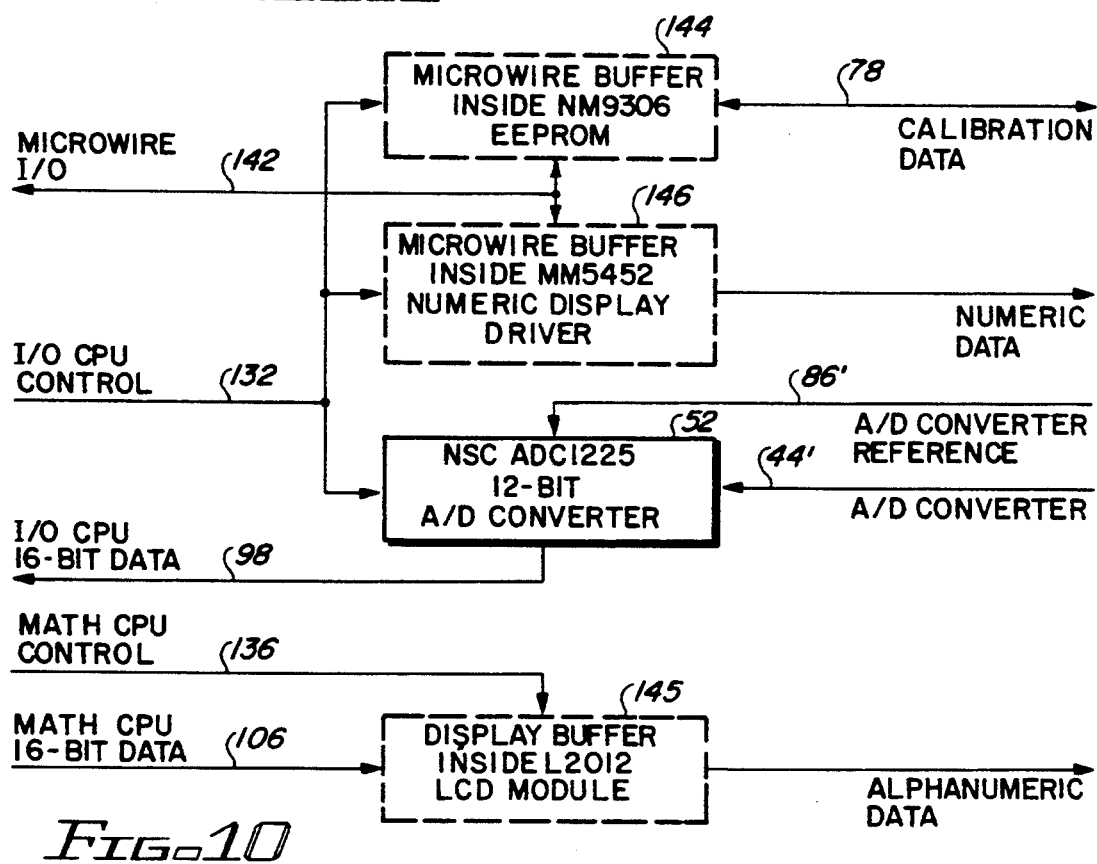
FIG. 10 is a block diagram of the input/output data path logic, including a twelve-bit analog-to-digital converter.

Within FIG. 10, additional components coupled to I/O CPU 108 and math CPU 120 are illustrated. Block 144 represents a microwire buffer within the EEPROM that is on-board the sensor module. As shown in FIG. 10, both Microwire I/O lines 142 and I/O CPU control lines 132 are coupled, via cable 42, to microwire buffer 144 to control the transmission of calibration data and other data to or from the EEPROM. Also shown in FIG. 10 is analog-to-digital converter 52 which is preferably a National Semiconductor twelve bit A/D converter available as Part Number ADC1225. As shown in FIG. 10, the A/D converter reference 86' generated by precision reference supply 86 (see FIG. 5) is provided to A/D converter 52. Also provided to A/D converter 52 is the analog output signal 44' generated by the selected sensor module and received by terminal 44 of cable 42. Finally, the I/O CPU control lines 132 are also provided to A/D converter 52 to signal when a conversion should be made. The raw, uncalibrated twelve-bit output of A/D converter 52 is coupled to the lower 12 bits of the 16-bit I/O CPU data bus 98 for further processing.

Within FIG. 1, display panel 40 is actually formed of an Epson brand 20 character L2012 LCD module and a 6 digit Epson LD-H7996AZ LCD module. The L2012 LCD module (not shown) includes an alphanumeric controller for receiving alphanumeric data, as well as X- and Y- drivers for causing the corresponding alphanumeric characters to be displayed. The 6 digit LD-H7996AZ LCD display (not shown) is driven by a pair of National Semiconductor MM5652 4½ digit controller/drivers for directly displaying numeric data.

With respect to the alphanumeric data to be displayed, the math CPU is used to control the data to be displayed. As shown in FIG. 10 the 16-bit math CPU data bus 106 and math CPU control lines 136 are coupled to a display buffer 145 within the L2012 LCD alphanumeric module Data latched in buffer 145 is then displayed as described above.

Actual displayed numeric data corresponding to measured values is controlled by I/O CPU 108. The MM5652 display drivers each include a Microwire buffer 146 for serial communications with the I/O CPU 108, and as shown in FIG. 10, the I/O CPU control lines and Microwire I/O decode lines 142 are coupled to the MM5652 Microwire buffer for sending data serially to the six-digit LCD display.

The manner in which the two CPUs 108 and 120 operate to access the selected sensor module and compute and display a measured value will now be described with reference to the flow diagram of FIG. 11. Box 150 represents a starting point in program control wherein the measuring meter 36 is initially switched on. Measuring meter 36 has an idle mode when it merely tests to determine whether a sensor module is connected, as by detecting the Sensor Present line. If the presence of a sensor is detected, the measuring meter proceeds to determine if the sensor module is valid, as by recognizing the sensor type and verifying that the calibration data points are within an expected range. If so, then the measuring meter is permitted to enter an active mode for making measurements.

When initially switched on, the measuring meter may perform a self-test, if desired, and then enters the idle mode. When in the idle mode, the measuring meter is at box 152 simply detects the Sensor Present line to see if a sensor module has been connected to cable 42. If not, program flow loops back to box 152. If a sensor module is present, the next step is to access the data stored in the EEPROM of the selected sensor module in the manner described above. If desired, identifying information, such as the sensor Serial Number, sensor type, and date of last calibration can be displayed as alphanumeric data on display panel 40, as indicated by box 154 in FIG. 11. Next, a check is made to determine whether the sensor type code accessed from the EEPROM of the sensor module is one of the sensor type codes to which the central processor is programmed to recognize; this step is represented by box 156. The I/O CPU ROM is programmed to include a database containing all possible sensor type codes to which the CPU can respond. If the sensor type code accessed from the sensor module does not match one of the valid sensor type codes stored in the database, the display panel displays a warning message and no measurements are permitted, as indicated by box 158. Assuming that a valid sensor type code has been read, program flow proceeds to box 160 wherein the calibration data points for the specified sensor type are compared to calibration data range values previously stored in a database of the central processor. Based on the sensor type code, the central processor determines the number of calibration data points stored in the EEPROM, and compares the relevant calibration data points stored in the sensor module EEPROM to minimum and maximum range values for the specified type of sensor. If the calibration points accessed from the sensor module are out of range, then program flow proceeds to box 162 for displaying a warning message on display panel 40 and preventing any measurements from being displayed. Assuming that the calibration data points are within the expected range, program flow proceeds to box 164, corresponding to the active mode of operation, wherein a valid sensor module is recognized.

In the active mode, program flow proceeds to box 166 wherein raw sensor data is accessed from the sensor module. This raw data could either be the analog output signal generated by the sensor module or parallel bits of digital data, as from a counter. If the raw data is an analog output signal, then the central processor activates the A/D converter to convert the analog signal to a 12-bit digital signal which is still in raw, uncalibrated form. The next step, indicated by box 168 is to convert the raw digital value to a calibrated measured value in accordance with calibration data points and interpolation algorithm associated with the particular sensor. One example of computing a measured value for a temperature sensor was already described above in conjunction with FIG. 2.

The next step in program flow is to set the number of significant digits to be displayed by the numeric display panel that displays the calibrated measured value. This step is D represented by box 170. The central processor derives from the Sensor Type word information including the family and class of the selected sensor module. Such information serves as an accuracy code to the central processor; either directly from such information, or via a look-up table in the central processor memory, the central processor determines the number of significant digits that should be displayed on the numeric measurement display to properly reflect the degree of accuracy of the selected sensor module. This information then determines which digits of the 6 digit LD-H7996AZ LCD display will be activated by the MM5652 4½ digit controller/drivers.

Program flow in FIG. 11 then proceeds to box 172 wherein the I/O CPU 108 causes the calibrated measured value to be displayed by the 6-digit numeric display. The last step in program flow is to again check if the sensor module is still present, as indicated by box 174. If the answer is yes, then the measuring meter remains active, and program flow returns to box 166 to obtain a new raw measurement from the sensor. If not, then the measuring meter returns to its idle mode, and program flow returns back to box 152 waiting for another sensor module to be connected.

Those skilled in the art will now appreciate that an improved instrumentation system has been described which permits a single hand-held computerized measurement meter to be used to display measurements taken by a wide variety of sensors. While the present invention has been described with respect to a preferred embodiment thereof, the description is for illustrative purposes only and is not to be construed as limiting the scope of the invention. Various modifications and changes may be made by those skilled in the art without departing from the true spirit and scope of the invention as defined by the appended claims.

APPENDIX A

I/O CPU MEMORY MAP

| Address Range | Definition | Function |
|---|---|---|
| FFFF:FFFE | Reset Vector | INTERRUPT VECTORS |
| FFFD:FFFC | NMI on I1 pin | |
| FFFB:FFFA | Ext. Interrupt on I2 pin | |
| FFF9:FFF8 | Ext. Interrupt on I3 pin | |
| FFF7:FFF6 | Ext. Interrupt on I4 pin | |
| FFF5:FFF4 | Timer Overflow or Underflow | |
| FFF3:FFF2 | UART/Ext. Interrupt on EXUI | |
| FFF1:FFF0 | EI pin External Interrupt | |
| FFEF:FFEE | JSRP Vectors | JSR VECTORS |
| FFED:FFEC | JSRP Vectors | |
| FFEB:FFEA | JSRP Vectors | |
| FFE9:FFE8 | JSRP Vectors | |
| FFE7:FFE6 | JSRP Vectors | |
| FFE5:FFE4 | JSRP Vectors | |
| FFE3:FFE2 | JSRP Vectors | |
| FFE1:FFE0 | JSRP Vectors | |
| FFDF:FFDE | JSRP Vectors | |
| FFDD:FFDC | JSRP Vectors | |
| FFDB:FFDA | JSRP Vectors | |
| FFD9:FFD8 | JSRP Vectors | |
| FFD7:FFD6 | JSRP Vectors | |
| FFD5:FFD4 | JSRP Vectors | |
| FFD3:FFD2 | JSRP Vectors | |
| FFD1:FFD0 | JSRP Vectors | |
| FFCF:FFCE to C001:C000 | EPROM Memory | USER MEMORY (16 Kbytes) |
| BFFF:BFFE Expansion Memory | EPROM | OPTIONAL USER MEMORY (16 Kbytes) |
| 7FFF:7000 to 4001:4000 | External RAM Memory | USER RAM (16 Kbytes) |
| 3FFF:3FFE to 2001:2000 | RAM Expansion Memory | OPTIONAL USER RAM (8 Kbytes) |
| 0BFF to 0800 | FIFO Communications Port (8 bit port) (any even byte in this range) | INTER-PROCESSOR COMMUNICATIONS |
| 07FF:07FE to 0400 | A to D Convertor Port (12 bit port) (any word addr in this range) | ADC PORT |
| 01FF:01FE to 01C1:01C0 | On Chip RAM (64 bytes) | |
| 0195:0194 | Watchdog Register | WATCHDOG LOGIC |
| 0192 | T0Con Register | TIMER BLOCK $T^0$-$T^3$ |
| 0191:0190 | TMMODE Register | |
| 018F:018E | DIVBY Register | |
| 018D:018C | $T^3$ Timer | |
| 018B:018A | R3 Register | |
| 0189:0188 | $T^2$ Timer | |
| 0187:0186 | R2 Register | |
| 0185:0184 | I2CR Register /R1 | |
| 0183:0182 | I3CR Register /$T^1$ | |
| 0181:0180 | I4CR Register | |
| 015F:015E | EICR Register | |
| 015C | EICON Register | |
| 0153:0152 | PORT P Output Register | TIMER BLOCK $T^4$-$T^7$ |
| 0151:0150 | PWMODE Register | |
| 014F:014E | R7 Register | |
| 014D:014C | $T^7$ Timer | |
| 014B:014A | B6 Register | |
| 0149:0148 | $T^6$ Timer | |
| 0147:0146 | R5 Register | |
| 0155:0144 | $T^5$ Timer | |
| 0143:0142 | R4 Register | |
| 0141:0140 | $T^4$ Timer | |
| 0128 | ENUR Register | UART |
| 0126 | TBUF Register | |
| 0124 | RBUF Register | |
| 0122 | ENUI Register | |
| 0120 | ENU Register | |
| 0104 | PORT D Input Register | PORT D |
| 00F5:00F4 | BFUN Register | PORTS A & B CONTROL |
| 00F3:00F2 | DIRB Register | |
| 00F1:00F0 | DIRA Register | |
| 00E6 | UPIC Register | UPI CONTROL |
| 00E3:00E2 | PORT B I/O Register | PORTS A & B |
| 00E1:00E0 | PORT A I/O Register/OBUF | |
| 00DE | Microcode ROM Dump Enable Register | PORT 1, CONTROL & 00DD:00DC Halt INTERRUPT CONTROL |
| 00D8 | PORT I Input Register | REGISTERS |
| 00D6 | SIO Register | |
| 00D4 | IRCD Register | |
| 00D2 | IRPD Register | |
| 00D0 | ENIR Register | |
| 00CF:00CE | X Register | HPC CORE REGISTERS |
| PPCD:00CC | B Register | |
| 00C8:00CA | K Register | |
| 00C9:00CB | A Register | |
| 00C7:00C6 | PC Register | |
| 00C5:00C4 | SP Register | |
| 00C3:00C2 | (reserved) | |
| 00C1:00C0 | PSW Register | |
| 00BF:00BE to 0001:0000 | On Chip RAM | USER RAM (192 bytes) |

APPENDIX B

GAL PROGRAMMING PROCEDURES

Outputs     Logic Equations

For Math CPU

APPENDIX B-continued

GAL PROGRAMMING PROCEDURES

| | | Outputs | Logic Equations |
|---|---|---|---|
| Memory High Byte Inputs | | | |
| HBEF, | CA23, | MSEH7F' | YF = HBEF'*A23'*A22'*A21'*A20'*A19'*A18' |
| CA22, | CA21, | MSEH6F' | YF = HBEF'*A23'*A22'*A21'*A20'*A19'*A18' |
| CA20, | CA19, | MSEH5F' | YF = HBEF'*A23'*A22'*A21'*A20'*A19*A18' |
| CA18, | CA17, | MSEH4F' | YF = HBEF'*A23'*A22'*A21'*A20'*A19*A18 |
| CA16, | CA15, | MSEH3F' | YF = HBEF'*A23'*A22'*A21'*A20*A19'*A18' |
| CA14, | CA13, | MSEH2F' | YF = HBEF'*A23'*A22'*A21'*A20*A19'*A18 |
| OEF, | ADSF | MSEH1F' | YF = HBEF'*A23'*A22'*A21'*A20*A19*A18' |
| IOADRHF' | | | YF = HBEF'*A23'*A22*A20'*A19'*A18'*A17'*A16'*A15'*A14'*A13' |
| Memory Low Byte Inputs | | | |
| CA0, | CA23 | MSEL7F' | YF = A-'*A23'*A22'*A21'*A20'*A19'*A18' |
| CA22, | CA21, | MSEL6F' | YF = A0'*A23'*A22'*A21'*A20'*A19'*A18 |
| CA20, | CA19, | MSEL5F' | YF = A0'*A23'*A22'A21'*A20*A19*A18 |
| CA18, | CA17, | MSEL4F' | YF = A0'*A23'*A22'*A21'*A20'*A19*A18 |
| CA16, | CA15, | MSEL3F' | YF = A0'*A23'*A22'*A21'*A20*A19'*A18 |
| CA14, | CA13, | MSEL2F' | YF = A0'*A23'*A22'*A21'*A20*A19'*A18 |
| OEF, | ADSF | MSEL1F' | YF = A0'*A23'*A22'*A21'*A20*A19*A18' |
| IOADRLF' | | | YF = A0'*A23'*A22*A21*A20'*A19'*A18'*A17'*A16'*A15'*A14'*A13' |

For I/O CPU

| | | Outputs | Logic Equations |
|---|---|---|---|
| I/O High Byte Inputs | | | |
| IOADRHF, | OEF, | IOSH7F' | YF = IOADRHF'*A11'*A10'*A9'*A8'*A7'*A6'*A5'*A4'*A3*A2*A1 |
| CA11, | CA10, | IOSH6F' | YF = IOADRHF'*A11'*A10'*A9'*A8'*A7'*A6'*A5'*A4'*A3*A2*A1' |
| CA9, | CA8, | IOSH5F' | YF = IOADRHF'*A11'*A10'*A9'*A8'*A7'*A6'*A5'*A4'*A3*A2'*A1 |
| CA7, | CA6, | IOSH4F' | YF = IOADRHF'*A11'*A10'*A9'*A8'*A7'*A6'*A5'*A4'*A3*A2'*A1' |
| CA5, | CA4, | IOSH3F' | YF = IOADRHF'*A11'*A10'*A9'*A8'*A7'*A6'*A5'*A4'*A3'*A2*A1 |
| CA3, | CA2, | IOSH2F' | YF = IOADRHF'*A11'*A10'*A9'*A8'*A7'*A6'*A5'*A4'*A3'*A2*A1' |
| CA1, | ADSF | IOSH1F' | YF = IOADRHF'*A11'*A10'*A9'*A8'*A7'*A6'*A5'*A4'*A3'*A2'*A1 |
| | | IOSH0F' | YF = IOADRHF'*A11'*A10'*A9'*A8'*A7'*A6'*A5'*A4'*A3'*A2'*A1' |
| I/O Low Byte Inputs | | | |
| IOADRLF, | OEF, | IOSL7F' | YF = IOADRLF'*A11'*A10'*A9'*A8,*A7'*A6'*A5'IA4'*A3*A2*A1 |
| CA11, | CA10, | IOSL6F' | YF = IOADRLF'*A11'*A10'*A9'*A8'*A7'*A6'*A5'*A4'*A3*A2*A1' |
| CA9, | CA8, | IOSL5F | YF = IOADRLF'*A11'*A10'*A9'*A8'*A7'*A6'*A5'*A4'*A3*A2'*A1 |
| CA7, | CA6, | IOSL4F | YF = IOADRLF'*A11'*A10'*A9'*A8'*A7'*A6'*A5'*A4'*A3*A2'*A1' |
| CA5, | CA4, | IOSL3F' | YF = IOADRLF'*A11'*A10'*A9'*A8'*A7'*A6'*A5'*A4'*A3'*A2*A1 |
| CA3, | CA2, | IOSL2F' | YF = IOADRLF'*A11'*A10'*A9'*A8'*A7'*A6'*A5'*A4'*A3'*A2*A1' |
| CA1, | ADSF | IOSL1F' | YF = IOADRLF'*A11'*A10'*A9'*A8'*A7'*A6'*A5'*A4'*A3'*A2'*A1 |
| | | IOSL0F' | YF = IOADRLF'*A11'*A10'*A9'*A8'*A7'*A6'*A5'*A4'*A3'*A2'*A1' |
| I/O CPU Inputs | | | |
| HBEF, | HA15, | HMEM1HF' | YF = HBEF'*A15*A14 |
| HA14, | HA13, | HMEM1LF' | YF = A0'*A15*A14 |
| HA12, | HA11, | HMEM2HF' | YF = A0'*A15*A14' |
| HA8, | HA7, | HRAMHF, | YF = HBEF'*A15'*A14 |
| HA6, | OEF, | HRAMLF' | YF = A0'*A15'*A14 |
| HA0, | ALE | HFIFOF' | YF = HBEF*A0'*A15'*A14'*A13'*A12'*A11*A10' |
| | | HADCF' | YF = A15'*A14'*A13'*A12'*A11'*A10 |

I claim:

1. A self-calibrating instrumentation apparatus for use with a plurality of sensor modules of different types for sensing and measuring a plurality of parameters; comprising in combination:

a. a first sensor module of a first sensor type including a first sensor responsive to a first condition for generating a first electrical signal indicative of such first condition, said first sensor module also providing a sensor type code for identifying said first sensor module as being of said first sensor type;

b. a second sensor module of a second sensor type different from said first sensor type and including a second sensor responsive to a second condition for generating a second electrical signal indicative of such second condition, said second sensor module also providing a sensor type code for identifying said second sensor module as being of said second sensor type;

c. central processor means responsive to electrical signals generated by said first sensor module and by said second sensor module for computing a measurement sensed by said first sensor module and by said second sensor module;

d. display means coupled to said central processor means for numerically displaying the measurement computed by said central processor means;

e. means for selectively coupling one of said first and second sensor modules to said central processor;

f. each of said first and second sensor modules including a memory;

g. the memory of said first sensor module storing calibration data indicative of the magnitude of the electrical signal generated by said first sensor module at first and second known conditions;

h. the memory of said second sensor module storing calibration data indicative of the magnitude of the electrical signal generated by said second sensor module at first and second known conditions;

i. said central processor means accessing and being responsive to the calibration data stored in the memory of the selected sensor module that is coupled to said central processor means for calibrating said central processor means when computing the measurement sensed by the selected sensor module, said central processor being further responsive to the sensor type code of the selected sensor module for selecting an algorithm used to compute the measured value of the parameter being sensed by the selected sensor module relative to the calibration data accessed from the memory of the selected sensor module, said central processor means computing the measurement sensed by said first sensor module in accordance with a first predetermined algorithm, and said central processor means computing the measurement sensed by said second sensor module in accordance with a second predetermined algorithm difference from the first predetermined algorithm.

2. The instrumentation apparatus recited by claim 1 wherein each of said first and second sensor modules provides its respective electrical signal as an analog signal, and wherein said central processor means includes an analog-to-digital converter for converting the analog signal to a digital signal.

3. The instrumentation apparatus recited by claim 1 wherein each of the memories of said first and second sensor modules stores said calibration data and said sensor type code as digital signals.

4. The instrumentation apparatus recited by claim 3 wherein each of the memories of said first and second sensor modules stores at least a first calibration data word at a first memory address and a second calibration data word at a second memory address, and wherein said central processor means addresses the memory of the selected sensor module to access both the first calibration data word and the second calibration data word.

5. The instrumentation apparatus recited by claim 3 wherein each of the memories of said first and second sensor modules is an erasable programmable memory for allowing each sensor module to be recalibrated at selected intervals.

* * * * *